United States Patent [19]
Tanaka et al.

[11] Patent Number: 5,763,795
[45] Date of Patent: Jun. 9, 1998

[54] SAMPLING APPARATUS

[75] Inventors: Yosuke Tanaka; Hiroyuki Seshimo, both of Kobe; Hidetoshi Nishimoto, Kakogawa; Yasuhiro Ooyama, Kobe, all of Japan

[73] Assignee: TOA Medical Electronics Co., Ltd., Hyogo, Japan

[21] Appl. No.: 770,049

[22] Filed: Dec. 19, 1996

[30] Foreign Application Priority Data

Dec. 19, 1995 [JP] Japan ................................. 7-350707

[51] Int. Cl.$^6$ ............................................. G01N 27/02
[52] U.S. Cl. ..................... 73/863.73; 324/439; 324/693; 324/705
[58] Field of Search ..................... 73/863.73, 864.83, 73/863.71; 324/71.4, 439, 442, 443, 444, 693.705; 128/734, 765, 766

[56] References Cited

U.S. PATENT DOCUMENTS

| | | | |
|---|---|---|---|
| 2,656,508 | 10/1953 | Coulter | 73/861.04 |
| 4,152,391 | 5/1979 | Cabrera | 73/864.83 |
| 4,891,575 | 1/1990 | Kogo et al. | 324/71.4 |
| 4,957,008 | 9/1990 | Proni et al. | 73/863.73 |
| 5,524,496 | 6/1996 | Nagai et al. | 73/863 |
| 5,542,305 | 8/1996 | Hollinger | 73/863.73 |

FOREIGN PATENT DOCUMENTS 213748 4/1984 Japan.

*Primary Examiner*—Ronald L. Biegel

[57] ABSTRACT

A sample apparatus includes a sampling valve having a sample inlet through which a sample such as urine is introduced from the outside of the sampling valve to the inside thereof; a sample outlet through which the sample is sent from the inside of the sampling valve to the outside thereof; and a sampling passage for setting apart a predetermined amount of the sample between the sample inlet and sample outlet. It further includes a first electrode section located close to the sample inlet so that the sample can come into contact with the first electrode section, a second electrode section located close to the sample outlet so that the sample can come into contact with the second electrode section, and a sensor circuit for measuring the impedance between the first and second electrode sections and for using the measured impedance to determine whether or not the sampling passage contains a predetermined amount of the sample. Preferably, the first and second electrode sections each include a pair of electrodes separated from each other, wherein one of each of the electrodes of the electrode sections is connected to the sensor circuit while the other electrodes are short-circuited to each other.

18 Claims, 7 Drawing Sheets

SAMPLING APPARATUS

BACKGROUND OF THE INVENTION

1. Technical Field of the Invention

The present invention pertains generally to a sampling apparatus and, more particularly, relates to a sampling apparatus which can detect existence or non-existence of an electrically conductive sample in a sampling valve and set apart a predetermined small amount of the sample with a high degree of accuracy for its analysis.

2. Description of the Related Art

A sampling valve is often used for sampling a predetermined small amount of a given sample such as urine, blood or the like by use of a sampling valve. In general, by driving a sample sucking pump connected to the sampling valve, a sample is introduced via a sample inlet into a sampling (measuring) passage for setting apart a predetermined amount of the sample which is formed in the sampling valve, and sent out of a sample outlet to a predetermined section, for example, a reactor.

Japanese Examined Patent Publication No. Hei 2(1990)-13748 discloses a sampling apparatus provided with a sensing system for sensing a shortage of sample which may occur due to intrusion of air bubbles into a sampling passage or clogging of the passage by constituents of the sample, for instance when a sample supplying pump is driven. The sensing system comprises a pair of optical sensors, each composed essentially of a light emitter and a photodetector. These optical sensors are installed close to a sample inlet pipe and a sample outlet pipe of a sampling valve and monitor at the inlet and outlet pipes the amount of light transmitted through the sample supplied in the sampling passage.

In the sampling apparatus disclosed in the above publication, the optical sensors sometimes do not detect the existence or non-existence of a sample due to the turbidity of the sample. For example, when handling urine samples which range from nearly transparent to highly turbid ones including cloudy urine and bloody urine, it is difficult to discriminate between a nearly transparent sample and air. It is also difficult to discriminate between residues of preceding samples attaching to an inside wall of the sampling pipe and a new sample introduced into the pipe. Furthermore, the sampling apparatus of the publication requires a complex construction because the pair of optical sensors, each comprising the light emitter and the photodetector, must be installed in the minute pipes of the apparatus in order to minimize variations in pipe diameter in the sampling valve and upstream and downstream pipes.

SUMMARY OF THE INVENTION

It is an object of the invention to provide a sampling apparatus which is intended to have an increased degree of accuracy in setting apart a predetermined amount of an electrically conductive sample as well as a simplified equipment construction.

According to the invention, a sampling apparatus comprises a sampling valve having a sample inlet through which an electrically conductive sample is introduced from the outside of the sampling valve to the inside thereof, a sample outlet through which the sample is sent from the inside of the sampling valve to the outside thereof and a sampling passage for setting apart a predetermined amount of the sample between the sample inlet and sample outlet, a first electrode section located near the sample inlet in such a manner that the first electrode section comes into contact with the sample, a second electrode section located near the sample outlet in such a manner the second electrode section comes into contact with the sample, and a measuring section for detecting a variation in the impedance between the first and second electrode sections.

Electrically conductive samples handled by the sampling apparatus of this invention may be liquid samples of which electrical conductivity ranges between 2 and 50 mS/cm (millisiemens per centimeter), for instance. Urine and blood are examples of such liquid samples.

The sample inlet and sample outlet of the sampling valve are openings at both ends of a flow path which constitutes the sampling passage. It is preferable that the sample inlet and sample outlet be formed at sample input and output portions of pipes which are connected to the sampling valve.

The two plate-like elements, for example, are a movable valve element and a fixed valve element which are preferably coaxially mounted in contact with each other so that they can be relatively rotated on a common axis. A liquid sample filled into the through holes formed in the individual valve elements is pushed out by a specific amount of diluent to deliver a liquid sample diluted at a predetermined ratio. In a case where the three plate-like elements are used, at least one element is the movable valve element relative to the remaining two elements. It is essential that the sampling valve be made of an insulating material. Preferably, the sampling valve has corrosion-resistance (chemical-resistance) as well as mechanical strength. Materials for the sampling valve include electrically nonconductive ceramic materials and engineering plastics.

According to the invention, the sampling passage may be a sampling through hole having a specific volumetric capacity that is formed in the sampling valve and/or a sampling tube connected to the body of the sampling valve.

In another preferred form of the invention, the first and second electrode sections are electrically connected by the electrically conductive sample fed in the sampling passage formed when the through-holes of the plate-like elements are in the communication position by the element moving mechanism.

In still another preferred form of the invention, the first and second electrode sections each include a pair of electrodes separated from each other, and one of the electrodes of each of the electrode sections is connected to the measuring section while the other electrodes are short-circuited to each other.

The pair of electrodes separated from each other mentioned above are two electrodes which can be electrically connected only by an electrically conductive sample present in the pipes joined to the sample inlet and sample outlet of the sampling valve. It is preferable that each pair of electrodes be connected to each other by a sleeve made of an insulating material. The two electrodes constituting each electrode pair may either be separated by a specific distance in a sample-flowing direction or located face to face in a direction perpendicular to the sample-flowing direction with a specific spacing therebetween. The distance between the two electrodes of each electrode pair may be determined as appropriate in accordance with characteristics of the electrically conductive sample, and particularly the average length of conductive solid constituents of the sample, density of the sample, wetting properties of the sleeve with respect to the sample's liquid, surface tension of the sample, etc. In a case where the sample handled by the apparatus is urine, it is desirable that the sleeve connecting the electrodes of each electrode pair have an inside diameter of 1 mm and the distance between the electrodes be set to 1.5 to 2.0 mm. for instance.

The measuring section of the invention comprises detecting means for comparing impedance measured between the first and second electrode sections with a reference impedance to detect that the sampling passage is filled with the predetermined amount of the sample when a difference arises between the measured impedance and the reference impedance.

The detecting means of the invention comprises an oscillation circuit for applying a pulse signal between the first and second electrode sections, a comparison circuit for forming signals corresponding to the measured impedance and the reference impedance from the applied pulse signal to compare amplitudes of the formed signals with each other, and a display section for displaying a comparison result by the comparison circuit, the comparison circuit outputting a control signal to ensure the sampling of the electrically conductive sample when a difference arises between the amplitudes, the display section showing that the sampling of the electrically conductive sample is ensured.

Further, the comparison circuit may output a control signal to allow a next operation when the sampling is ensured.

A component used for short-circuiting the electrodes located close to the sampling valve should preferably be made of a good conductor.

In still another preferred form of the invention, the first and second electrode sections each include a pair of electrodes separated from each other in a direction to which the electrically conductive sample flows, the electrode of each of the electrode sections which is located farther from the sampling valve is connected to the measuring section while the other electrodes of the electrode sections which are closer to the sampling valve are short-circuited to each other.

In still another preferred form of the invention, the first and second electrode sections each include a pair of electrodes separated from each other, and one of the electrodes of each of the electrode sections is connected to the measuring section while the other electrodes are selectively short-circuited to or disconnected from each other.

A mechanism for selectively short-circuiting and disconnecting the latter electrodes may be constructed with a relay of which contacts are connected and disconnected in response to switching control signals fed from a controller, for instance.

The electrically conductive sample is urine, for example. The urine sample handled by the apparatus may be raw or diluted by a reagent or a diluent.

In the sampling apparatus of the invention, the sample inlet of the sampling valve is connected to a sampling pipette while the sample outlet is connected to a reaction chamber, for instance. A specific amount of an electrically conductive sample fed from the sampling pipette is introduced into the sampling valve by way of the first electrode section and the sample inlet and fills the first electrode section, the sampling passage and the second electrode section. At this point, the sensor circuit measures the impedance between the first electrode section located close to the sample inlet and the second electrode section located close to the sample outlet and compares the value of the measured impedance with a reference impedance value which represents the value of the impedance between the two electrodes measured when they are completely isolated from each other.

A difference arising between the measured impedance value and reference impedance value suggests that the first and second electrode sections have been electrically connected to each other through the sample. If such a difference in impedance is found, it is judged that the electrically conductive sample has filled a fluid passage including the sample inlet, sampling passage and sample outlet. In this case, the sensor circuit can output a signal indicating that the amount of sample is appropriate based on the judgment result.

On the contrary, if no difference is found between the measured impedance value and reference impedance value, it is most likely that the first and second electrode sections have not been electrically connected to each other. Should this situation occur, it is judged that there exists air, in the form of bubbles for example, in the fluid passage, that is, the sampling passage has not been filled with the proper amount of electrically conductive sample. In this case, the sensor circuit can output a signal indicating that the amount of sample is inadequate based on the judgment result.

With this method of sample detection based on impedance variations, it is possible to overcome the earlier-mentioned problems of the conventional sample detection method which uses optical sensors. Specifically, it becomes easier to discriminate between a true sample and air even when handling urine samples which range from nearly transparent to highly turbid ones including cloudy urine and bloody urine. False detection of samples that can occur due to variations in their turbidity in the conventional optical method can therefore be avoided. The sample detection method of the invention also makes it easy to discriminate between residues of preceding samples attaching to an inside wall of a sample-carrying pipe and a new sample introduced into the pipe. Furthermore, since each sensing section is composed essentially of a pair of electrodes, it is possible to simplify mechanical construction and minimize variations in pipe diameter at the sampling valve and its upstream and downstream sides.

According to the construction in which the first and second electrode sections each include a pair of electrodes separated from each other and one electrode of each of the electrode sections is connected to the sensor circuit while the other electrodes are short-circuited to each other, an electrically conductive sample is introduced through the sample inlet into the sampling valve and the sampling passage at first. Then, the sensor circuit determines the impedance between one electrode of the first electrode section which is located at the sample inlet and one electrode of the second electrode section which is located at the sample outlet, and compares the value of the measured impedance with the reference impedance value.

A difference arising between the measured impedance value and reference impedance value suggests that each pair of electrodes of the first and second electrode sections have been electrically connected by the sample. If such a difference in impedance is found, it is judged that the electrically conductive sample has filled the fluid passage including the sample inlet, sampling passage and sample outlet. In this case, the sensor circuit can output a signal indicating that the amount of sample is appropriate based on the judgment result.

On the contrary, if no difference is found between the measured impedance value and reference impedance value, it is most likely that at least one pair of electrodes of the first and second electrode sections are not yet electrically connected by the sample. This suggests that air exists within the fluid passage. Should this situation occur, it is judged that the fluid passage has not been filled with the proper amount of electrically conductive sample. In this case, the sensor circuit can output a signal indicating that the amount of sample is inadequate based on the judgment result.

This construction provides sensitivity high enough for detecting samples having low electrical conductivity.

According to the construction in which the first and second electrode sections each include a pair of electrodes separated from each other in the sample-flowing direction and the electrodes located far from the sampling valve are individually connected to the sensor circuit while the electrodes located close to the sampling valve are short-circuited to each other, no electrical wiring is required between the sampling valve and the sensor circuit. This is because the sensor circuit is connected only to the electrodes located far from the sampling valve, and not to those electrodes which are close to the sampling valve and integrally assembled therewith, when sample-carrying pipes are joined to the sampling valve at the individual electrode sections. Therefore, the construction of the apparatus is simplified and maintenance of the sampling valve is made easier, just requiring removal of the pipes prior to servicing.

According to the construction in which the first and second electrode sections each include a pair of electrodes separated from each other and one electrode of each of the electrode sections is connected to the sensor circuit while the other electrodes can be selectively short-circuited to or disconnected from each other, it is possible to handle samples having a wide range of electrical conductivity. This is because the sensor circuit can selectively determine the impedance all the way along the sampling passage or across the electrode sections. Furthermore, this construction helps identify a specific region where the sample is absent or insufficient.

The invention enables detection of a wide variety of electrically conductive samples including urine samples ranging from nearly transparent to cloudy and/or bloody urine. It can provide a sampling apparatus featuring an increased degree of accuracy in setting apart a predetermined amount of an electrically conductive sample as well as simplified equipment construction.

These and other objects of the present application will become more readily apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE PREFERRED EMBODIMENTS

FIGS. 1 to 4 shows part of the construction of a urinary corporeal element determination system 10 provided with a sampling apparatus according to an embodiment of the invention.

Figure 1:
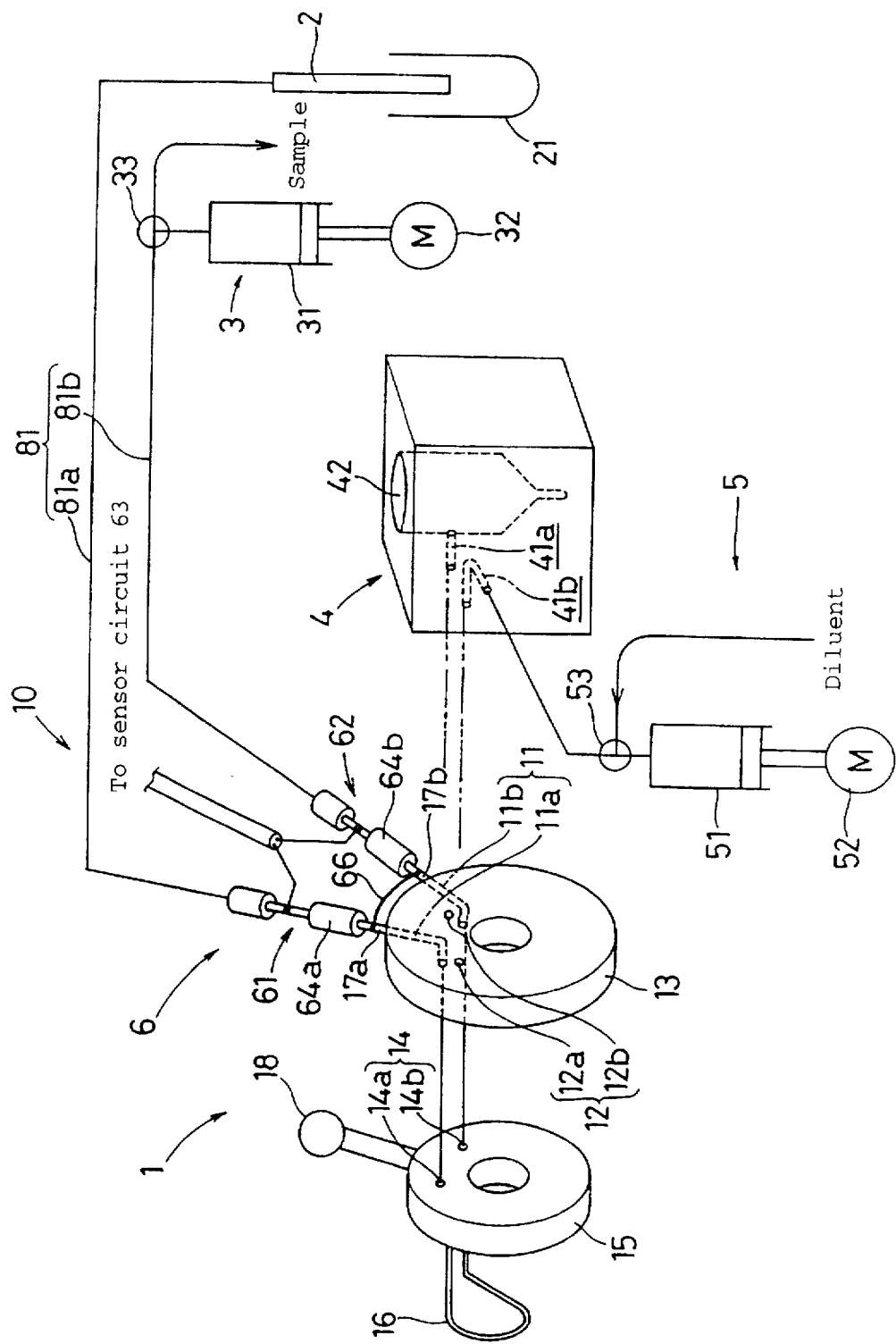
FIG. 1 is a diagram generally illustrating a status in which a urinary corporeal element determination system according to an embodiment of the invention is sucking a urine sample.

The urinary corporeal element determination system 10 mainly comprises a sampling valve 1, a sampling pipette 2, a sample sucker 3, a reaction chamber 4, a diluent feeder 5 and a sample sensing section 6 as shown in FIG. 1.

The sampling valve 1 is composed principally of a large-diameter predetermined valve element 13 having through hole pairs 11, 12, etc. which allow samples to pass through, a small-diameter rotary valve element 15 having a plurality of through hole pairs 14, etc. corresponding to the through hole pairs 11, 12, etc. and a sampling tube 16 which connects to the through hole pairs 14. Both the predetermined valve element 13 and the rotary valve element 15 are disklike components made by forming an electrically non-conductive ceramic material. These valve elements 13, 15 are coaxially mounted in contact with each other so that they can be relatively rotated on a common axis. Contact surfaces of the two valve elements 13, 15 are held tight against each other to prevent liquid leaks. Individual through holes 11a and 11b constituting the through hole pair 11 of the predetermined valve element 13 are through holes, each having an opening in the contact surface of the predetermined valve element 13 and another opening in its cylindrical outer surface. The through holes 11a and 11b are therefore bent within the predetermined valve element 13 at generally right angles. The openings of the through holes 11a and 11b in the cylindrical outer surface of the predetermined valve element 13 serve as a sample inlet 17a and outlet 17b. The through hole pairs 12 and 14 are formed parallel to the common axis of the valve elements 13 and 15 and have respective openings in the contact surfaces of the valve elements 13 and 15.

Openings of the through hole pair 12 on the other side of the predetermined valve element 13 are connected to the reaction chamber 4 while openings of the through hole pair 14 on the other side of the rotary valve element 15 are connected to the sampling tube 16. The through hole pair 14 can be selectively connected to the through hole pair 11 or 12 by turning a changeover lever 18 fitted to the cylindrical outer surface of the rotary valve element 15.

Tubular electrodes of the later-described sample sensing section 6 are inserted into the sample inlet 17a and outlet 17b of the predetermined valve element 13, and the sample inlet 17a and outlet 17b are connected to the sampling pipette 2 and sample sucker 3 by pipes 81 (81a, 81b), respectively.

The sampling pipette 2 is made movable relative to a sample rack located at a sampling position so that the sampling pipette 2 can successively take samples out of urine test tubes 21 mounted on the sample rack. The sample sucker 3 comprises a sample sucking syringe 31 which is connected to the pipe 81b via a three-way directional control valve 33 as well as a syringe driver 32.

The reaction chamber 4 is composed principally of a chamber block having inner channels 41a and 41b. The reaction chamber 4 is held in contact with one side surface of the predetermined valve element 13. One end of the channel 41a opens in a side wall of a cavity 42 in the chamber block while the channel 41b is connected to the diluent feeder 5. The diluent feeder 5 comprises a diluent feeding syringe 51 which is connected to the channel 41b via a three-way directional control valve 53 as well as a syringe driver 52.

Figure 2:
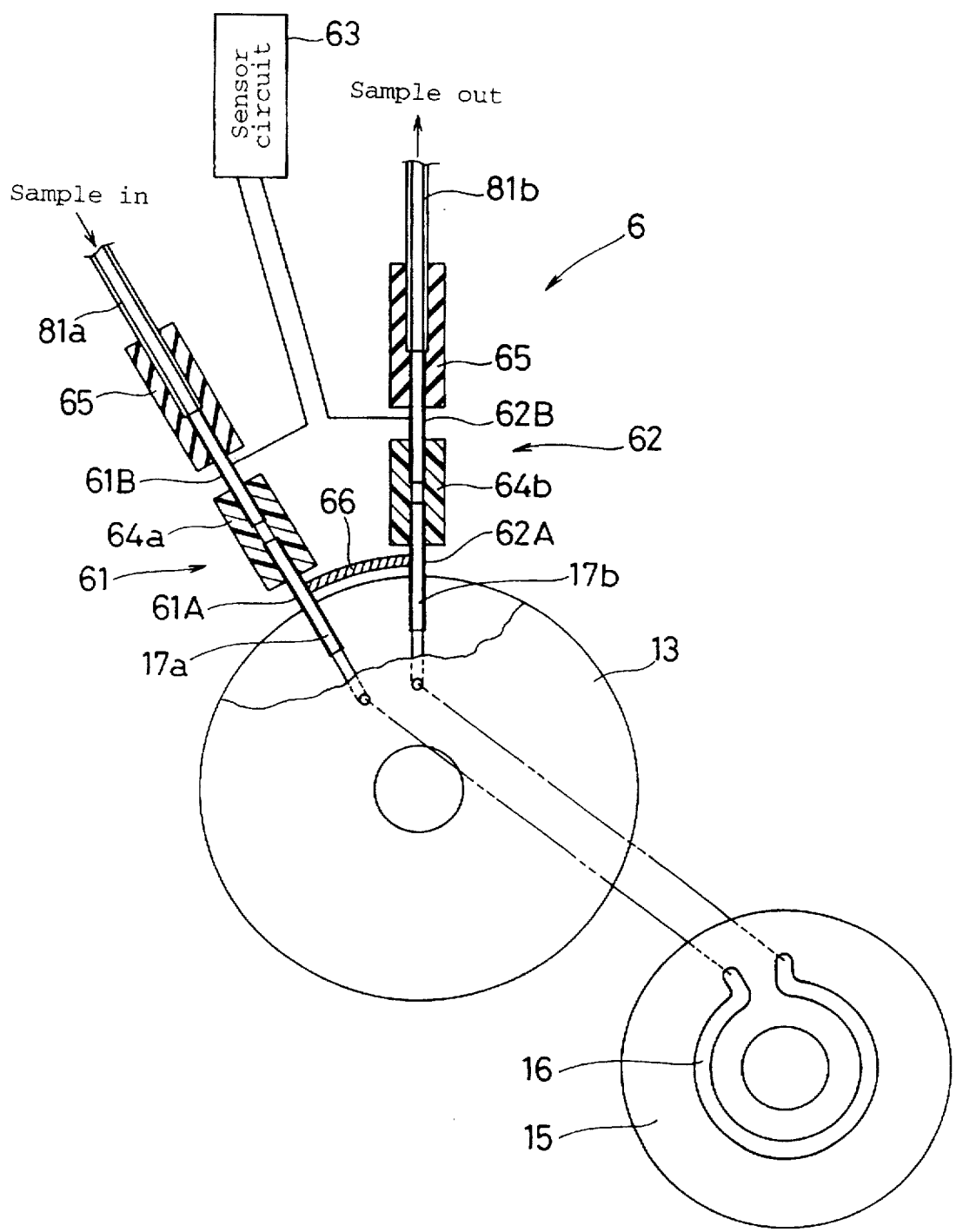
FIG. 2 is a diagram illustrating a sample sensing section of the urinary corporeal element determination system of FIG. 1.

The sample sensing section 6 is composed principally of a first electrode section 61 located in the vicinity of the sample inlet 17a of the predetermined valve element 13, a second electrode section 62 located in the vicinity of the sample outlet 17b and a sensor circuit 63 as shown in FIG. 2.

The first electrode section 61 comprises an electrode pair including a tubular electrode 61A inserted into the sample inlet 17a and a tubular electrode 61B mounted separately from the tubular electrode 61A at the upstream side thereof. The tubular electrodes 61A and 61B are connected to each other by a insulating sleeve 64a made of polytrifluoro ethylene. The pipe 81a, tubular electrode 61B, sleeve 64a and tubular electrode 61A form together a tubular passageway having an approximately equal inside diameter that connects the sampling pipette 2 and the sample inlet 17a to each other.

The second electrode section 62 comprises an electrode pair including a tubular electrode 62A inserted into the sample outlet 17b and a tubular electrode 62B mounted separately from the tubular electrode 62A at the downstream side thereof. The tubular electrodes 62A and 62B are connected to each other by a insulating sleeve 64b made of polytrifluoro ethylene. The tubular electrode 62A, sleeve 64b and tubular electrode 62B form together a tubular passageway having an approximately equal inside diameter that connects the sample outlet 17b to the pipe 81b.

Made of stainless steel SUS316, each tubular electrode has an outside diameter of 1.5 mm, an inside diameter of 1.0 mm and a length of about 10 mm. The sleeves 64a and 64b securely connect the tubular electrodes 61A and 61B, and the tubular electrode 62A and 62B, respectively, so that the distance between them are held at 1.5 to 2.0 mm. The tubular electrodes 61B and 62B are connected to the pipes 81a and 81b by rubber joints 65, respectively.

Figure 4:
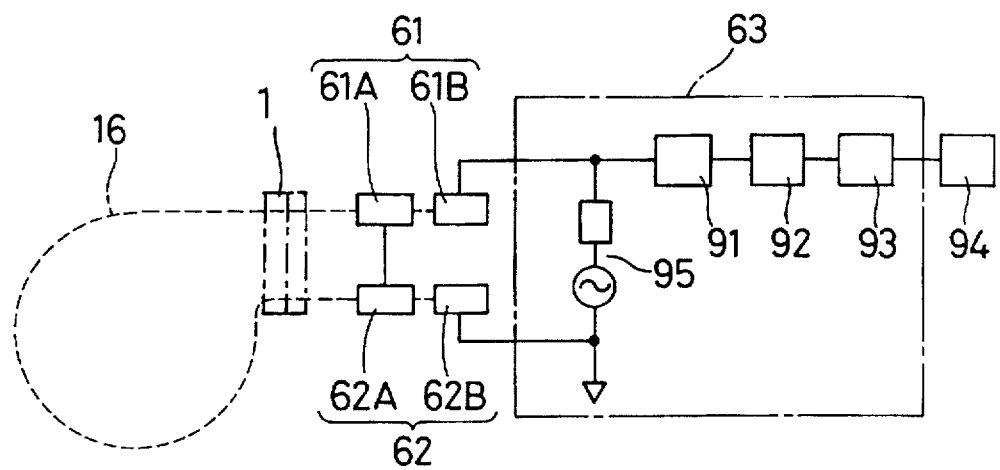
FIG. 4 is a block diagram of the sample sensing section according to the aforementioned embodiment.

The tubular electrode 61B of the first electrode section 61 and the tubular electrode 62B of the second electrode section 62 located far from the sampling valve 1 are individually connected to the sensor circuit 63 while the tubular electrodes 61A and 62A located close to the sampling valve 1 are short-circuited to each other by a piece of conductor 66. FIG. 4 is a simplified block diagram of the urinary corporeal element determination system 10. The sensor circuit 63 comprises an oscillator 95, an amplifier 91, a detector 92, a comparator 93 and a display 94, and is connected to an unillustrated controller.

Operation of the urinary corporeal element determination system 10 is now described with reference to FIGS. 1 to 4. It is now assumed that a specimen taken from raw urine is used as an electrically conductive sample. Referring first to FIG. 1 which shows a status where a urine sample is being sucked, the changeover lever 18 of the sampling valve 1 is operated in order to connect the through hole pair 14 of the rotary valve element 15 to the through hole pair 11 of the predetermined valve element 13. When the sample sucking syringe 31 is connected to the pipe 81b by the three-way directional control valve 33, the syringe driver 32 is activated and a predetermined amount of urine sample is sucked by the sampling pipette 2 from one urine test tube 21 and is delivered toward the sample inlet 17a.

When the urine sample reaches the sample outlet 17b and pipe 81b by way of the pipe 81a, sample inlet 17a and sampling tube 16, the sensor circuit 63 is activated and it detects whether the urine sample is present or not. The sensor circuit 63 measures the impedance between the tubular electrode 61B and tubular electrode 62B and measurement results are sent to a comparator 93. Then, the comparator 93 compares the value of the measured impedance reference impedance with a value which represents the value of the impedance between the two electrodes measured when they are completely isolated from each other.

A difference arising between the measured impedance value and reference impedance value suggests that both the sleeve 64a and the sleeve 64b have been filled with the urine sample, which acts as a conducting medium placed between the tubular electrodes 61A and 61B of the first electrode section 61, and between the tubular electrode 62A and 62B of the second electrode section 62. If such a difference in impedance is found, it is judged that the predetermined amount of urine sample has filled a fluid passage including the sample inlet 17a, sampling tube 16 and sample outlet 17b. In this case, the comparator 93 outputs a signal to a display 94 indicating that the current urine sample is properly prepared and does not interrupt preparation of a next urine sample.

On the contrary, if no difference is found between the measured impedance value and reference impedance value, it is most likely that the tubular electrodes 61A and 61B of the first electrode section 61 and/or the tubular electrode 62A and 62B of the second electrode section 62 are still isolated from each other because the sleeve 64a or sleeve 64b, or both, are not filled with the urine sample. Should this situation occur, it is judged that the urine sample has not fully filled the fluid passage including the sample inlet 17a, sampling tube 16 and sample outlet 17b. In this case, the comparator 93 outputs a signal to the display 94 indicating that the amount of the current urine sample is insufficient, causes the current urine sample to be excluded from measurement, and then outputs a signal to the controller requesting it to re-execute preparation of a urine sample taken from the same urine test tube 21.

Figure 3:
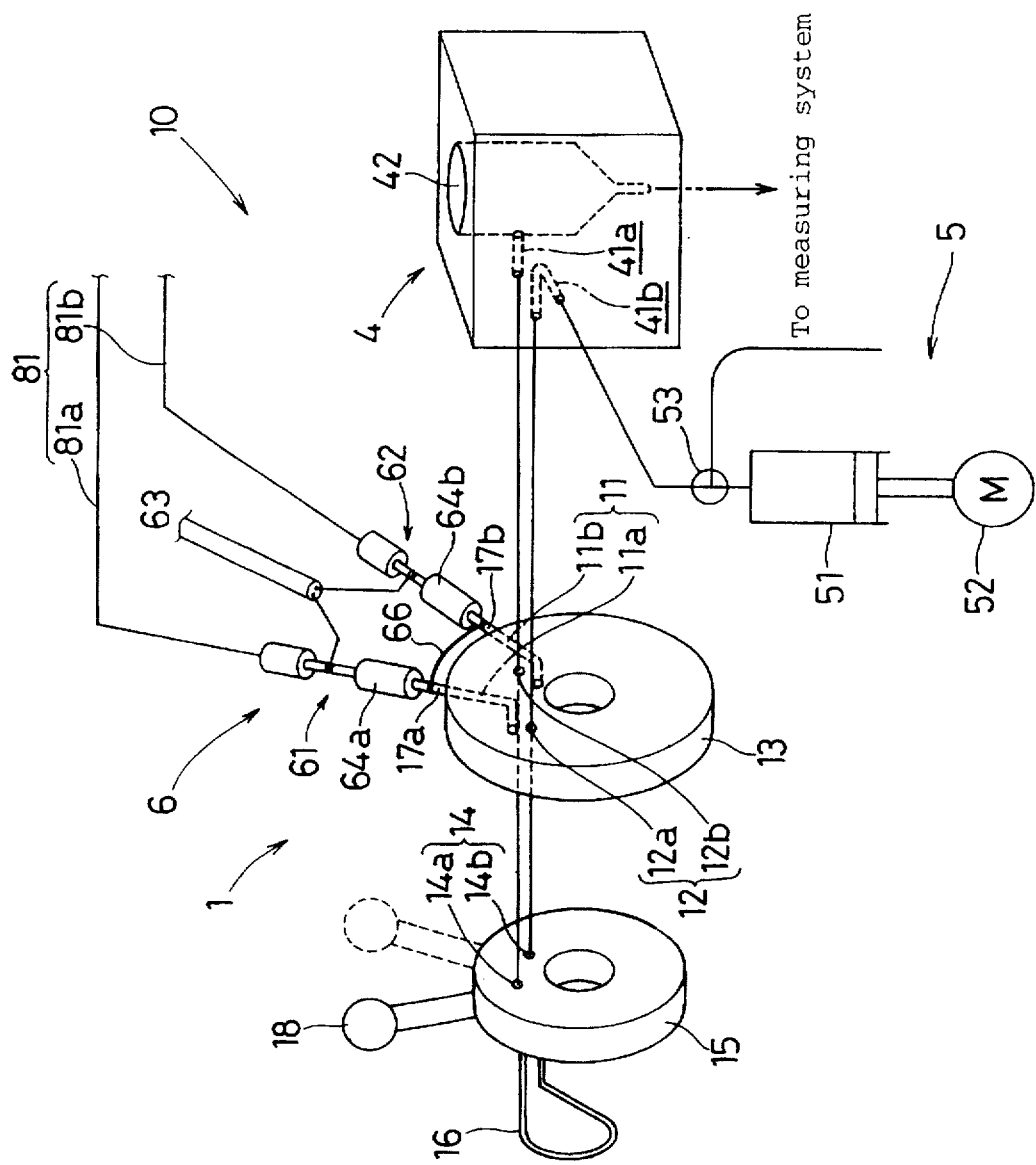
FIG. 3 is a diagram similar to FIG. 1 generally illustrating a status in which the urinary corporeal element determination system is delivering the urine sample.

In a case where it is judged by the sensor circuit 63 that the current urine sample is properly prepared, the changeover lever 18 of the sampling valve 1 is operated to connect the through hole pair 14 of the rotary valve element 15 to the through hole pair 12 of the predetermined valve element 13 as shown in FIG. 3. Consequently, a predetermined amount of the urine sample that is contained in the internal space of the through hole pair 14 of the rotary valve element 15 and the sampling tube 16 is separated from the other part of the urine sample. When the three-way directional control valve 53 of the diluent feeder 5 is activated and the diluent feeding syringe 51 is connected to the channel 41a of the reaction chamber 4 via the channel 41b and through hole pair 12, the syringe driver 52 is activated and a predetermined amount of diluent is sent from the diluent feeding syringe 51 so that the urine sample remaining in the through hole pair 14 and sampling tube 16 is discharged into the reaction chamber 4 together with the diluent. As a result, the urine sample diluted at a predetermined ratio is fed into the reaction chamber 4 and then the diluted urine sample is delivered to a measuring system for executing a urinary sediment test (quantitative determination of corporeal elements in urine).

Figure 5:
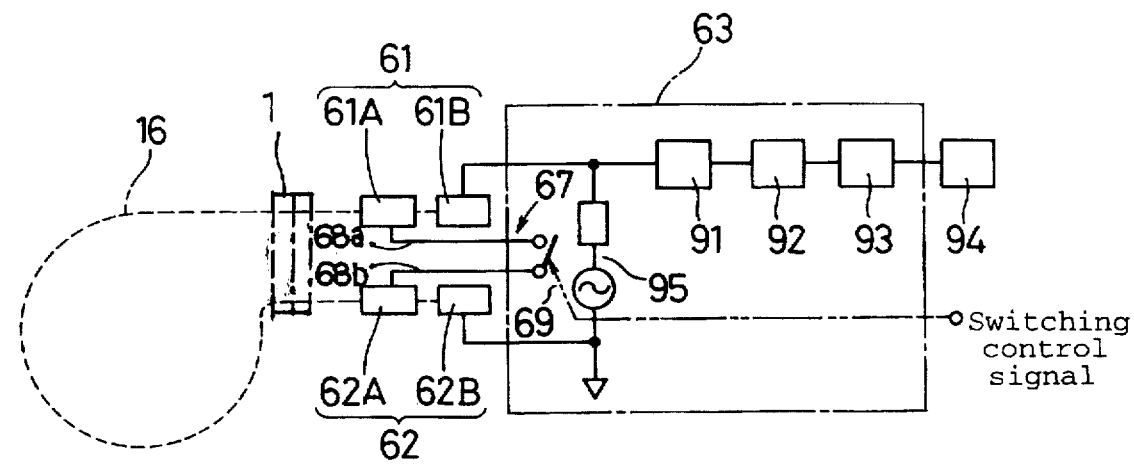
FIG. 5 is a block diagram similar to FIG. 4 illustrating a sample sensing section according to an alternative embodiment.

FIG. 5 is a block diagram showing a circuit configuration according to an alternative embodiment, in which one of two electrodes of each electrode section (first electrode section 61 and second electrode section 62) is connected to a sensor circuit 63 while the other electrodes of the two electrode sections 61, 62 can selectively be closed or opened. In the configuration of FIG. 5, the electrodes 61B and 62B located far from the sampling valve 1 are individually connected to the sensor circuit 63 in the same way as the foregoing embodiment while the electrodes 61A and 62A located close to the sampling valve 1 are connected to a switching device 67 which substitutes for the aforementioned fixed conductor 66.

The switching device 67 includes leads 68 (68a, 68b) connected to the electrodes 61A and 62A and a relay 69 of which contacts are connected and disconnected in accordance with switching control signals fed from the controller.

In one sample detection mode performed by this circuit configuration as illustrated in FIG. 5, a urine sample is detected with the contacts of the relay 69 connected in the beginning. As discussed earlier with reference to the foregoing embodiment, a difference arising between a measured impedance value and reference impedance value suggests that both the sleeve 64a and the sleeve 64b have been filled with the urine sample, which acts as a conducting medium placed between the tubular electrodes 61A and 61B of the first electrode section 61, and between the tubular electrode 62A and 62B of the second electrode section 62. If such a difference in impedance is found, it is judged that the urine sample has filled a fluid passage including the sample inlet 17a, sampling tube 16 and sample outlet 17b.

On the contrary, if the sensor circuit 63 judges that there is no difference between the measured impedance value and reference impedance value, the contacts of the relay 69 are disconnected and the sensor circuit 63 performs a second cycle of sample detection. If there is still no difference between the measured impedance value and reference impedance value, it can be regarded that the sleeve 64a and sleeve 64b are not filled with the urine sample. If, however, a difference is found between the measured impedance value and reference impedance value in the second detection cycle, it can be regarded that the urine sample has filled the sleeves 64a and 64b as well as the sampling tube 16. Therefore, the circuit configuration of this alternative embodiment makes it possible to detect existence or non-existence of the urine sample in a reliable manner.

In another sample detection mode performed by the above circuit configuration as illustrated in FIG. 5, a urine sample is detected with the contacts of the relay 69 disconnected in the beginning. If a difference is found between the measured impedance value and reference impedance value, it is judged that the urine sample has filled the sleeves 64a and 64b as well as the sampling tube 16.

On the contrary, if the sensor circuit 63 judges that there is no difference between the measured impedance value and reference impedance value, the contacts of the relay 69 are connected and the sensor circuit 63 performs a second cycle of sample detection. If there is still no difference between the measured impedance value and reference impedance value, it can be regarded that the sleeve 64a and sleeve 64b are not filled with the urine sample, and not that the electrical conductivity of the urine sample is low.

A difference arising between the measured impedance value and reference impedance value in the second detection cycle suggests that the sleeves 64a and 64b are filled with a urine sample having a low electrical conductivity. In this case, it is judged that the urine sample has filled the fluid passage including the sample inlet 17a, sampling tube 16 and sample outlet 17b. It is therefore possible to the detect existence or non-existence of the urine sample in a reliable manner regardless of the electrical conductivity of individual urine samples.

Figure 6:
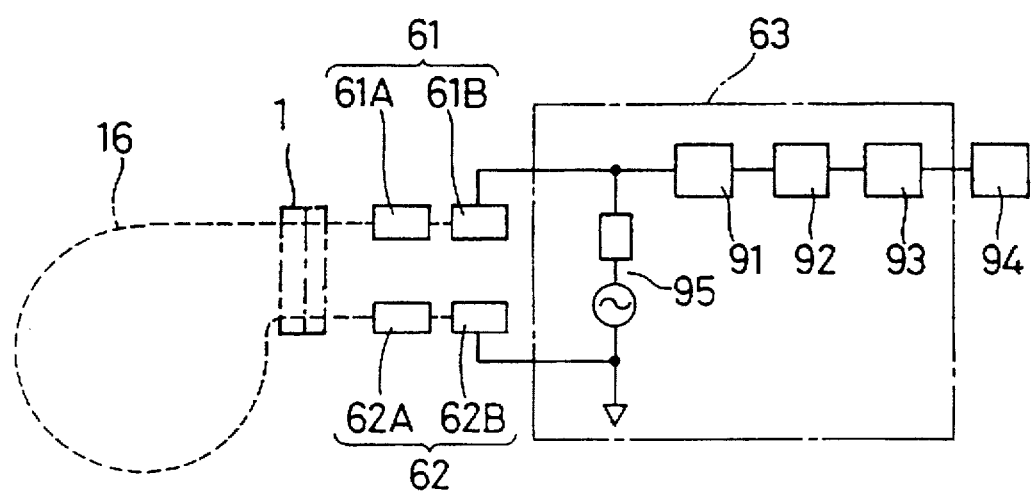
FIG. 6 is a block diagram similar to FIG. 4 illustrating a sample sensing section according to a still alternative embodiment.

FIG. 6 is a block diagram showing a circuit configuration according to a still alternative embodiment, in which one of two electrodes of each electrode section (first electrode section 61 and second electrode section 62) is connected to a sensor circuit 63. In this embodiment, the other electrodes of the two electrode sections 61, 62 are not connected to each other by a predetermined conductor 66, but only the electrodes 61B and 62B located far from the sampling valve 1 are individually connected to the sensor circuit 63.

If no difference is found between a measured impedance value and reference impedance value in a urine sample detection cycle, it can be regarded that the sleeve 64a, sleeve 64b or sampling tube 16 is not filled with the urine sample. If a difference is found between the measured impedance value and reference impedance value, it can be regarded that the urine sample has filled the sleeves 64a and 64b as well as the sampling tube 16. It is therefore possible to detect existence or non-existence of the urine sample in a reliable manner.

Figure 7:
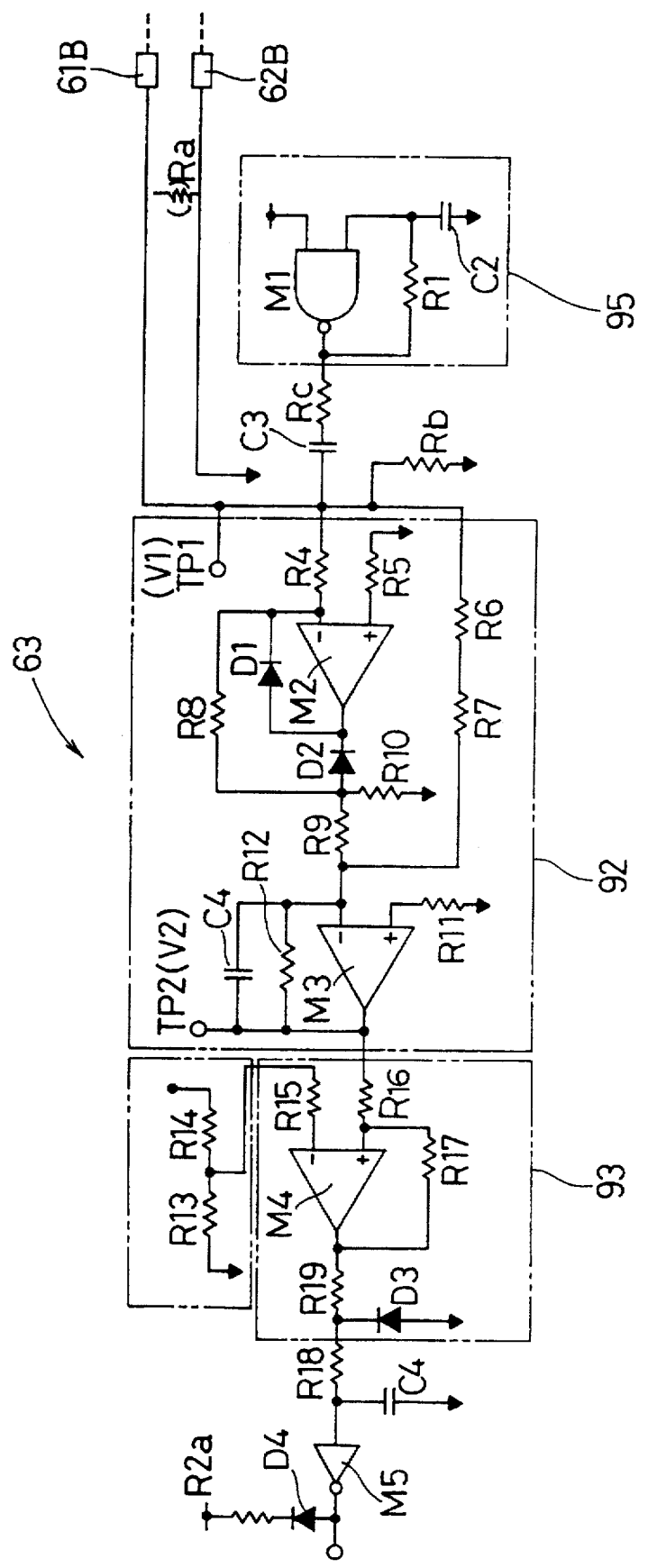
FIG. 7 is a circuit diagram of a sensor circuit of a sample sensing section according to one form of embodiment of the invention.

Shown in FIG. 7 is a specific circuit diagram of a sensor circuit 63, in which a capacitor C3 is connected in series with a resistor Rc and a resistor Rb is connected in parallel with a resistor Ra which is connected between two electrodes 61B and 62B. This sensor circuit 63 is intended to enable reliable detection of air bubbles. Values of these components may be properly selected so that a pulse signal V1 appearing at a test point TP1 shows maximum variations depending on whether a urine sample is present at the electrodes. As an example, the resistors Rb, Rc and the capacitor C3 are set to 220 k$\Omega$, 33 k$\Omega$ and 0.047 $\mu$F, respectively. Also, a resistor R1 and a capacitor C2 are set to 100 k$\Omega$ and 0.015 $\mu$F, respectively. Designated by M1 is a complementary metal oxide semiconductor (CMOS) type Schmitt trigger NAND gate.

Figure 8:
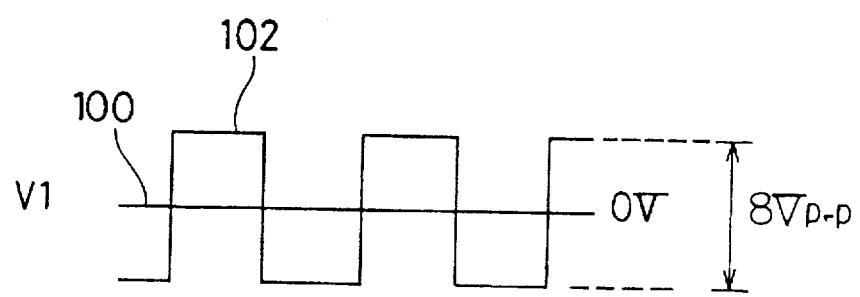
FIG. 8 shows a waveform of a signal V1 appearing at a test point TP1 of the sensor circuit of FIG. 7.
Figure 9:
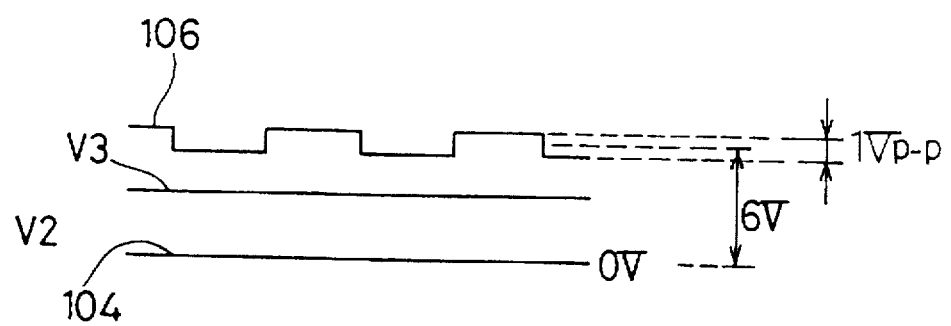
FIG. 9 shows a waveform of a signal V2 appearing at a test point TP2 of the sensor circuit of FIG. 7.

FIGS. 8 and 9 show a waveform of the pulse signal V1 appearing at the test point TP1 and a waveform of a pulse signal V2 appearing at a test point TP2, respectively. The frequency of these pulse signals V1, V2 is 2.0 kHz, for instance. In FIG. 8, the numeral 100 indicates the level of the signal V1 observed when a sample is present while the numeral 102 indicates the same when there is not any sample except for air. In FIG. 9, the numeral 104 indicates the level of the signal V2 observed when a sample is present while the numeral 106 indicates the same when there is not any sample except for air. The signal V1 demodulated by a wave detector 92 is compared with a predefined voltage V3 in a comparator 93, of which output is expressed by two binary values depending on whether or not a sample is present. With the circuit configuration of FIG. 7, it is possible to measure electrical conductivity between 2 and 38 mS/cm.

According to the above-described embodiments and their alternatives, the electrodes are provided close to the sample inlet 17a and sample outlet 17b of the sampling valve 1 to which the sampling tube 16 is connected. An AC signal is applied to the electrodes and variation in the amplitude of a signal appearing between the electrodes are detected in accordance with the electrical conductivity (impedance) of a urine sample. It is possible to determine the existence or non-existence of the urine sample in a reliable manner regardless of its turbidity since a predetermined amount of the urine sample is separated and subsequent testing thereof is allowed only when the measured impedance value exceeds the reference impedance value.

The sleeves 64a and 64b are made of polytrifluoro ethylene having low wetting properties in this invention. This construction serves to prevent a problem of a residue of previous urine samples, wherein a new urine sample, supplied in only a small amount merely sticking to the inside walls of the sleeves 64a and 64b, is detected as a real sample when the sleeves 64a and 64b are not actually filled with a urine sample.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A sampling apparatus comprising:
a sampling valve including a sample inlet, through which an electrically conductive sample is input, a sample outlet through which the electrically conductive sample is output, and a sampling passage connected between the sample inlet and sample outlet;
a first electrode section located near the sample inlet;
a second electrode section located near the sample outlet; and
a measuring section for measuring an impedance between the first and second electrode sections and for comparing the measured impedance to a reference impedance to determine whether or not the sampling passage contains a predetermined amount of the sample.

2. A sampling apparatus according to claim 1 wherein the measuring section includes an oscillation circuit for applying a pulse signal between the first and second electrode sections, a comparison circuit for forming signals corresponding to the measured impedance and the reference impedance from the applied pulse signal and for comparing amplitudes of the formed signals, and a display section for displaying a result of the amplitude comparison by the comparison circuit.

3. The sampling apparatus of claim 1, wherein the first and second electrode sections contact the sample.

4. The sampling apparatus of claim 1, wherein each of the first and second electrode sections include a pair of electrodes insulated from each other.

5. The sampling apparatus of claim 4, wherein one of the pair of electrodes of each of the first and second electrode sections are connected to the measuring section and the other one of the pair of electrodes of each of the first and second electrode sections are short-circuited.

6. The sampling apparatus of claim 4, wherein a first of the pair of electrodes of the first electrode section is connectable to a tube for channeling the sample into the sampling inlet and a first of the pair of electrodes of the second electrode section is connectable to a tube for channeling the sample from the sampling outlet.

7. The sampling apparatus of claim 1, wherein the first electrode section is insertable in the sampling inlet and the second electrode section is insertable in the sampling outlet.

8. A sampling apparatus comprising:
a sampling valve including a sample inlet, through which an electrically conductive sample is input, a sample outlet through which the electrically conductive sample is output, and a sampling passage connected between the sample inlet and sample outlet;
a first electrode section located near the sample inlet;
a second electrode section located near the sample outlet; and
a measuring section for detecting a variation in impedance between the first and second electrode sections, wherein the sampling valve further includes,
at least two plate-like elements, each having at least one contact surface and a through hole, at least one opening of the through hole being formed on the contact surface;
element moving means for relatively moving the plate-like elements to a communication position in which the through holes of the plate-like elements communicate with each other via the openings on the contact surfaces and to a discommunication position in which the through holes of the plate-like elements discommunicate with each other, retaining the plate-like elements in liquid-tight contact with each other via the contact surfaces thereof; and
liquid flow means for introducing liquid from the sample inlet into the through holes with the plate-like elements in the communication position and for sending the liquid out of the sample outlet.

9. A sampling apparatus according to claim 8 wherein the two plate-like elements each include at least one pair of through holes so disposed that openings of the through holes on the contact surface face and openings of the through holes of the other plate-like element on the contact surface align when the two plate-like elements are in the communication position, the other openings of the pair of through holes of one plate-like element respectively define the sample inlet and the sample outlet, and the pair of through holes of the other plate-like element communicate with each other.

10. A sampling apparatus according to claim 8 wherein the first and second electrode sections are electrically connected by the sample fed in the sampling passage formed when the through-holes of the plate-like elements are moved into the communication position by the element moving means.

11. A sampling apparatus according to claim 8, wherein the measuring section includes an oscillation circuit for applying a pulse signal between the first and second electrode sections, a comparison circuit for forming signals corresponding to the measured impedance and the reference impedance from the applied pulse signal and for comparing amplitudes of the formed signals, and a display section for displaying a result of the amplitude comparison by the comparison circuit.

12. The sampling apparatus of claim 8, wherein the first and second electrode sections contact the sample.

13. A sampling apparatus comprising:
a sampling valve including a sample inlet through which an electrically conductive sample is input, a sample outlet through which the electrically conductive sample is output, and a sampling passage connected between the sample inlet and sample outlet;
a first electrode section located near the sample inlet;
a second electrode section located near the sample outlet; and
a measuring section for detecting a variation in impedance between the first and second electrode sections, wherein the first and second electrode sections each include a pair of electrodes separated from each other, and wherein one of the electrodes of each of the first and second electrode sections is connected to the measuring section and the other electrode of each of the first and second electrode sections are short-circuited.

14. A sampling apparatus according to claim 13, wherein the measuring section includes an oscillation circuit for applying a pulse signal between the first and second electrode sections, a comparison circuit for forming signals corresponding to the measured impedance and the reference impedance from the applied pulse signal and for comparing amplitudes of the formed signals, and a display section for displaying a result of the amplitude comparison by the comparison circuit.

15. The sampling apparatus of claim 13, wherein the first and second electrode sections contact the sample.

16. A sampling apparatus comprising:

a sampling valve including a sample inlet through which an electrically conductive sample is input, a sample outlet through which the electrically conductive sample is output, and a sampling passage connected between the sample inlet and sample outlet;

a first electrode section located near the sample inlet;

a second electrode section located near the sample outlet; and a measuring section for detecting a variation in impedance between the first and second electrode sections, wherein the first and second electrode sections each include a pair of electrodes separated from each other in a direction to which the sample flows, the electrode of each of the first and second electrode sections which is located relatively farther from the sampling valve is connected to the measuring section and the other electrodes of the first and second electrode sections, which are relatively closer to the sampling valve, are short-circuited.

17. A sampling apparatus comprising:

a sampling valve including a sample inlet through which an electrically conductive sample is input, a sample outlet through which the electrically conductive sample is output, and a sampling passage connected between the sample inlet and sample outlet;

a first electrode section located near the sample inlet;

a second electrode section located near the sample outlet; and a measuring section for detecting a variation in impedance between the first and second electrode sections, wherein the first and second electrode sections each include a pair of electrodes separated from each other, one of the pair of electrodes of each of the first and second electrode sections being connected to the measuring section and the other electrodes being selectively short-circuited to or disconnected from each other.

18. A sampling apparatus according to any of claims 1 or 2 to 17, wherein the sampling apparatus is for sampling urine.

* * * * *